(12) United States Patent
Clavaud

(10) Patent No.: US 7,263,443 B2
(45) Date of Patent: Aug. 28, 2007

(54) COMPUTING WATER SATURATION IN LAMINATED SAND-SHALE WHEN THE SHALE ARE ANISOTROPIC

(75) Inventor: Jean-Baptiste Clavaud, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 10 days.

(21) Appl. No.: 11/251,329

(22) Filed: Oct. 14, 2005

(65) Prior Publication Data
US 2006/0085135 A1    Apr. 20, 2006

Related U.S. Application Data

(60) Provisional application No. 60/618,668, filed on Oct. 14, 2004.

(51) Int. Cl.
*G01V 3/38* (2006.01)

(52) U.S. Cl. ............................................. 702/7; 702/12

(58) Field of Classification Search .................... 702/7, 702/11, 12; 703/10
See application file for complete search history.

(56) References Cited

U.S. PATENT DOCUMENTS 6,493,632 B1* 12/2002 Mollison et al. ................ 702/2
2005/0114029 A1   5/2005 Clavaud et al.

OTHER PUBLICATIONS

Shray, Frank et al., Evaluation of Laminated Formations Using Nuclear Magnetic Resonance and Resistivity Anisotropy Measurements, SPE 72370, Oct. 2001, pp. 1-17.

* cited by examiner

*Primary Examiner*—Donald E McElheny, Jr.
(74) *Attorney, Agent, or Firm*—Bryan L. White; Kevin P. McEnaney; Jaime Castano

(57) ABSTRACT

A method to determine water saturation of laminated sand-shale formations based on measurements of formation and shale resistivity anisotropy, the fraction of shale, and the porosity.

16 Claims, 4 Drawing Sheets

COMPUTING WATER SATURATION IN LAMINATED SAND-SHALE WHEN THE SHALE ARE ANISOTROPIC

CROSS-REFERENCE TO RELATED APPLICATIONS

This application claims priority, under 35 U.S.C. § 119, to Provisional Application Ser. No. 60/618,668, filed Oct. 14, 2004, incorporated by reference in its entirety.

BACKGROUND OF THE INVENTION

1. Field of Invention

This invention pertains to techniques for determining characteristics of earth formations and, more particularly, to techniques to determine water saturation in laminated shale-sand formations from measurements of resistivity anisotropy.

2. Related Art

Electrical anisotropy has been used to detect low-resistivity, low-contrast pay zones such as can occur in thin-bed formations. A water-wet formation with large variability in grain size can be highly anisotropic in the oil-bearing portion and isotropic in the water-bearing portion. The resistivity anisotropy is generally attributed to grain-size variations that affect irreducible water saturation between the laminations. Thin, interbedded sandstones, siltstones, and mudstones have been modeled in which the models contain, for example, layers of low-permeability mudstone and layers of permeable sandstone with variable clay content. The simulated resistivity data are generally described as either perpendicular resistivity, meaning measured with current flowing perpendicular to the bedding, or parallel resistivity, meaning measured with current flowing parallel to the bedding. Plotting perpendicular resistivity versus parallel resistivity for a given interval provides an indication of how hydrocarbon saturation influences electric anisotropy (see FIG. 1).

An algorithm to compute water saturation in thin-bedded formations has been suggested in which the inputs include the horizontal resistivity, the vertical resistivity, the fine-grained volumetric fraction, and the water resistivity. In this approach, the thin bed is considered to be a bi-modal system having both coarse grain layers and fine grain layers. Knowing the horizontal and vertical resistivity and the amount of fine-grain material (from NMR measurement, for example), one can calculate the resistivity of the coarse grain and fine grain layers. One can then calculate the amount of water in each layer using, for example, Archie's law (with m and n equal to 2), and then the total amount of water and oil in the system by volumetric computation. This algorithm is summarized in FIG. 2. Again, this model assumes the system is a dual system (coarse grain and fine grain), the fraction of each material is known, the average porosity for the two layer types is equal, and the water resistivity is known.

A limitation of those two approaches is that they assume each layer is individually isotropic (i.e., $R_v$ and $R_h$ are equal in each layer). Recent log data acquired in laminated shale-sand formations indicate that in fact shale can be anisotropic.

SUMMARY

The present invention provides for the determination of water saturation of laminated sand-shale formations based on measurements of formation and shale resistivity anisotropy, the fraction of shale, and the porosity.

Advantages and other features of the invention will become apparent from the following description, drawings, and claims.

DETAILED DESCRIPTION

Figure 1:
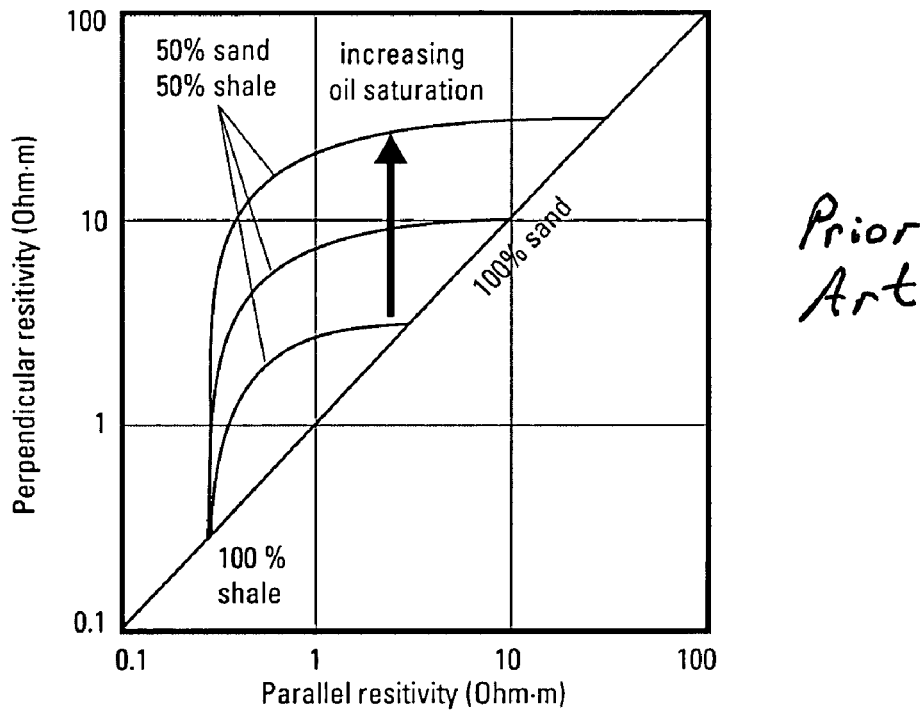
FIG. 1 is a prior art graph of perpendicular resistivity versus parallel resistivity.
Figure 2:
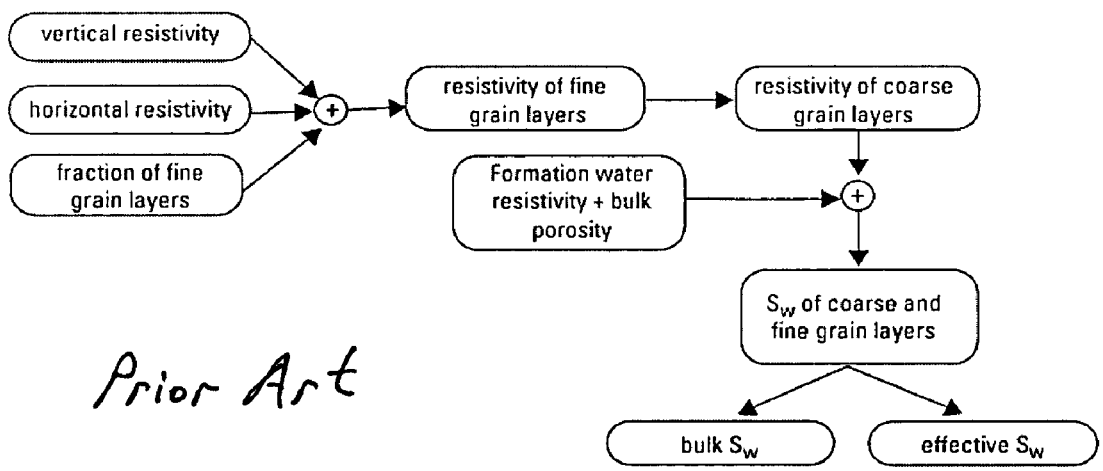
FIG. 2 shows a prior art method to compute water saturation without accounting for anisotropy.

The present invention is a modeling method using a set of equations during or after logging operations to take into account the intrinsic electrical anisotropy of shale when computing water saturation in laminated shale-sand formations. The computation of water saturation in earth formations is useful at least for pay/reserve quantification, oil/water contact detection, relative permeability estimation, and reservoir simulation.

The method makes use of anisotropy of resistivity measurements. The computation allows one to take the shale anisotropy into account to better estimate water saturation $S_w$. The computation is based on the inversion of the anisotropy of resistivity in thin-bedded laminated sand-shale in terms of shale and sand resistivities. A shale anisotropy term is used to obtain the correct resistivity for both the sand and the shale. Consequently, the correct water saturation $S_w$ can be computed for the sand, the shale, and the (total) formation.

Thinly laminated formations can be significant hydrocarbon reservoirs. Often such formations are anisotropic and exhibit the classical "low resistivity pay". Very large anisotropy of resistivity (say, larger than 3) can be due to the presence of water-bearing thin beds such as shale, for example, and oil-bearing sand layers. Electrical anisotropy can also arise from the shale structure. Shale are clay-rich formations, and because clay minerals are intrinsically laminated and anisotropic, shale are often anisotropic themselves.

One can model the anisotropy of resistivity of thinly laminated sand-shale formation when the shale are anisotropic. There are various known ways of determining the anisotropy of resistivity (Rv/Rh) of earth formations. These include, for example, resistivity logging tools (3D or conventional) and high-resolution resistivity imager averaging tools. There are also various known ways to determine the volumetric fraction of shale in an earth formation such as nuclear magnetic resonance logging tools, high-resolution resistivity imagers, spectroscopy logging tools, gamma ray logging tool, and nuclear logging tools. Nuclear magnetic resonance logging tools and nuclear logging tools can also be used to determine the total porosity of an earth formation.

To be clear on the meaning of various terms used herein, the following definitions are provided. "Thinly laminated" means a formation having lamination smaller than the resolution of the logging tool used to make the anisotropy of resistivity measurement. "Sand", unless otherwise indicated in the text, shall refer to "clean sand", meaning with little or no dispersed clay or conductive minerals, having good permeability, and with low irreducible water saturation. "Shale" refers to very fine sediment with large amounts of clay mineral, having poor permeability, and with irreducible water saturation close to 100%. For modeling purposes, it shall be assumed that each individual sand layer is a homogeneous and isotropic medium and each individual shale layer is a homogenous and anisotropic medium.

The model comprises a stack of layers (e.g., interspersed layers of sand and shale) having an average total porosity $\phi_T$ and water saturation $S_{wt}$ that obey the set of equations:

$$\phi_T = f_{shale} \cdot \phi_{shale} + (1 - f_{shale}) \cdot \phi_{sand} \quad (1)$$

$$S_{wt} = \frac{f_{shale} \cdot S_{w-shale} \cdot \phi_{shale} + (1 - f_{shale}) \cdot S_{w-sand} \cdot \phi_{sand}}{\phi_t} \quad (2)$$

Here $f_{shale}$ and $(1-f_{shale})$ are respectively the volume fraction of shale and sand. The shale are anisotropic and the ratio between the vertical shale resistivity and the horizontal shale resistivity is defined as the shale anisotropy $\alpha$ and is given by the following formula:

$$\alpha = \frac{R_{shale-v}}{R_{shale-h}} \quad (3)$$

Figure 3:
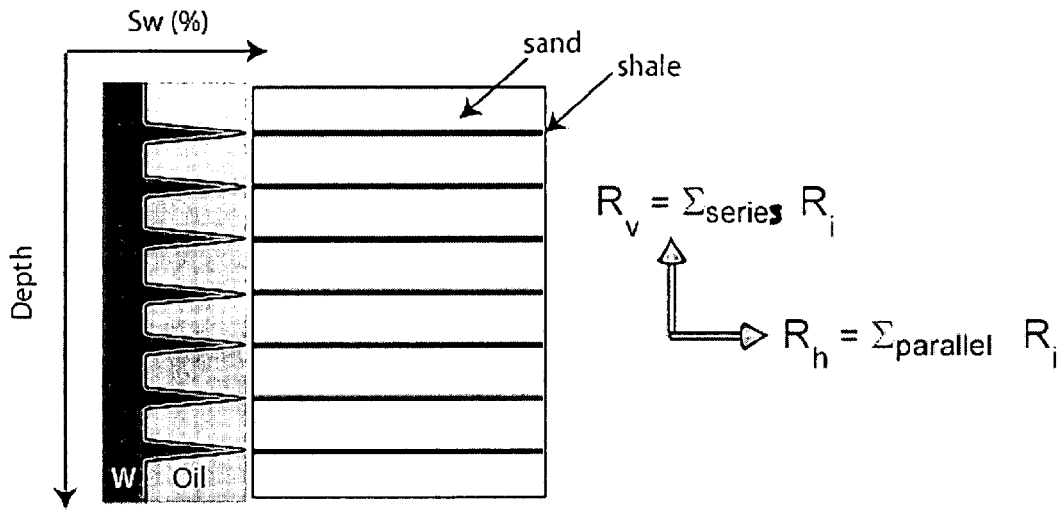
FIG. 3 shows a schematic view of a sand-shale formation model.

The mixing laws for the resistivity of a stack of layers are described in terms of series and parallel models (see FIG. 3). The averaging is a classic arithmetic mean and a harmonic mean. However, because the shale are considered anisotropic, the vertical resistivity of the shale is used when computing the vertical resistivity of the formation, and the horizontal resistivity of the shale is used when computing the horizontal resistivity of the formation. This leads to:

$$R_v = f_{shale} \cdot R_{shale-v} + (1 - f_{shale}) \cdot R_{sand} = \quad (4)$$
$$f_{shale} \cdot \alpha \cdot R_{shale-h} + (1 - f_{shale}) \cdot R_{sand}$$

$$R_h = \frac{R_{sand} \cdot R_{shale-h}}{f_{shale} \cdot R_{sand} + (1 - f_{shale}) \cdot R_{shale-h}} \quad (5)$$

We can solve this set of two equations if we know (e.g., have measured) the fraction of shale. The solution for the resistivity of the sand is:

$$R_{sand} = \frac{R_v + R_h \cdot (1 - f_{shale})^2 - \alpha \cdot R_h \cdot f_{shale}^2 \pm \sqrt{[R_v + R_h \cdot (f_{shale} \cdot (f_{shale} \cdot (1 - \alpha) - 2) + 1)]^2 - 4 \cdot (1 - f_{shale})^2 \cdot R_h \cdot R_v}}{2(1 - f_{shale})} \quad (6)$$

and the horizontal resistivity of the shale is:

$$R_{shale-h=} = \frac{R_v - R_h \cdot (1 - f_{shale})^2 + \alpha \cdot R_h \cdot f_{shale}^2 \pm \sqrt{[R_v + R_h \cdot (f_{shale} \cdot (f_{shale}(\alpha - 1) + 2) - 1)]^2 - 4 \cdot \alpha \cdot f_{shale}^2 \cdot R_h \cdot R_v}}{2 \cdot \alpha \cdot f_{shale}} \quad (7)$$

To choose the sign of the square root term in equation (6) and (7), one must know when the term inside the square root is equal to zero. An analysis of the square root terms in equation (6) and (7) leads to a limit for the horizontal resistivity noted $R_{h-limit}$:

$$R_{h-limit} = \frac{R_{shale}^2}{f_{shale} \cdot \alpha \cdot R_{shale-h} + R_{shale-h} \cdot \sqrt{\alpha \cdot (1 - f_{shale})^2}} \quad (8)$$

When $R_h \leq R_{h-limit}$, then the negative sign (−) should be used in equation (6) and the positive sign (+) should be used in equation (7). Similarly, when $R_h > R_{h-limit}$, then the positive sign (+) should be used in equation (6) and the negative sign (−) should be used in equation (7).

Once the horizontal resistivity of the shale and the resistivity of the sand have been computed, then the water saturation in the shale and sand can be estimated using known water saturation equations such as dual water, Waxman-Smits, or Archie's law. For example if we use Archie's law, the water saturation in the shale and the sand derived using the resistivities computed with equations (6) and (7) are:

$$S_{w-sand}^{-n_{sand}} = \frac{R_{sand}}{R_w \cdot \phi_{sand}^{-m_{sand}}} \quad (9)$$

$$S_{w-shale}^{-n_{shale}} = \frac{R_{shale-h}}{R_w \cdot \phi_{shale}^{-m_{shale}}} \quad (10)$$

where $R_w$ is the formation water resistivity, $\phi_{shale}$ and $\phi_{sand}$ are the porosity of the shale and the sand, and $n_{sand}$, $n_{shale}$, $m_{sand}$, and $m_{shale}$ are the Archie exponents for the sand and the shale.

Figure 4:
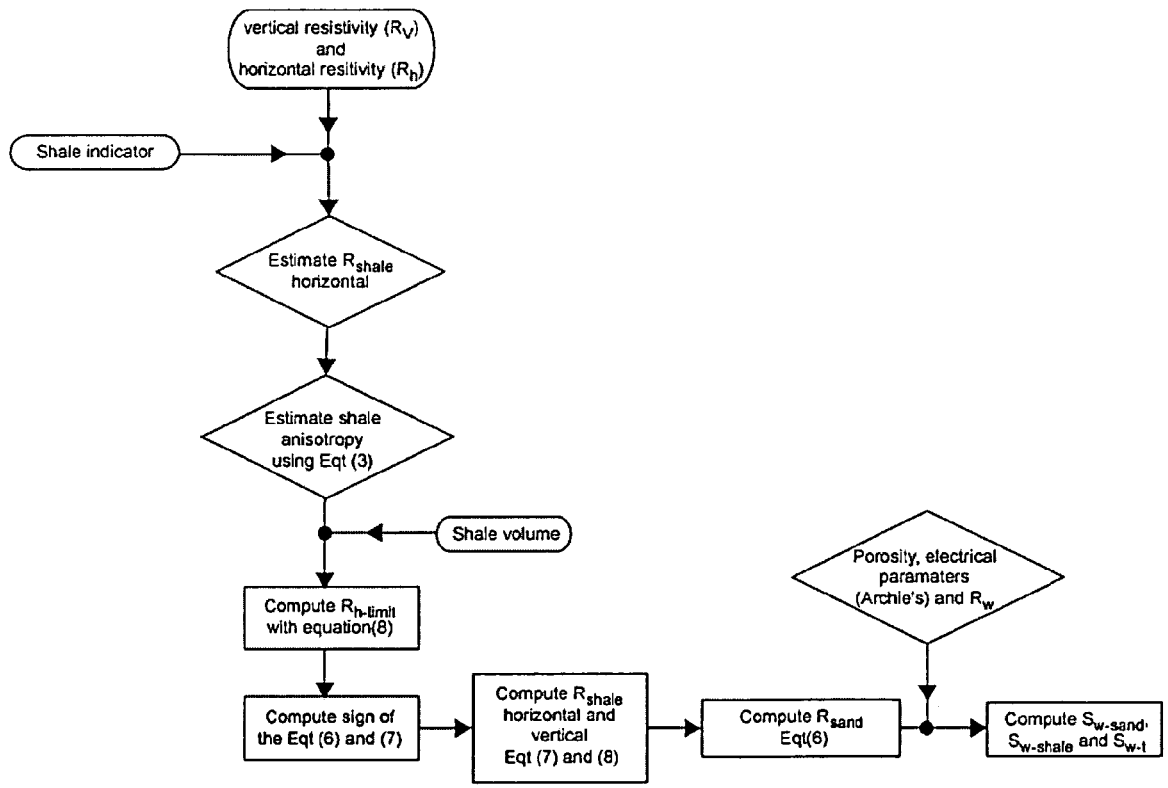
FIG. 4 is a flowchart showing the steps taken in accordance with the present invention.

The work flow for this invention and the necessary parameters/computations is summarized in FIG. 4.

To further demonstrate the method, an example is provided using forward modeling to show the effect of shale anisotropy on the water saturation computation when the shale anisotropy is equal to 2 and 3, and when the fraction of shale is equal to 0.5. The underlying assumptions are:

formation water resistivity equals 0.09 ohm-m;
(clean) sand porosity equals 0.3 with water saturation ranging from 0.1 to 1 and
Archie parameters m equal to 1.8 and n equal to 2; and
shale porosity equals 0.3 with water saturation equal to 1, and Archie's parameters m equal to 2.2 and n equal to 2.

The model yields a sand resistivity between 0.78 ohm-m and 78 ohm-m. The horizontal shale resistivity is 1.27 ohm-m, and the vertical shale resistivity is 2.54 ohm-m and 3.81 ohm-m, respectively, when the shale anisotropy is 2 and 3.

Figure 5A:
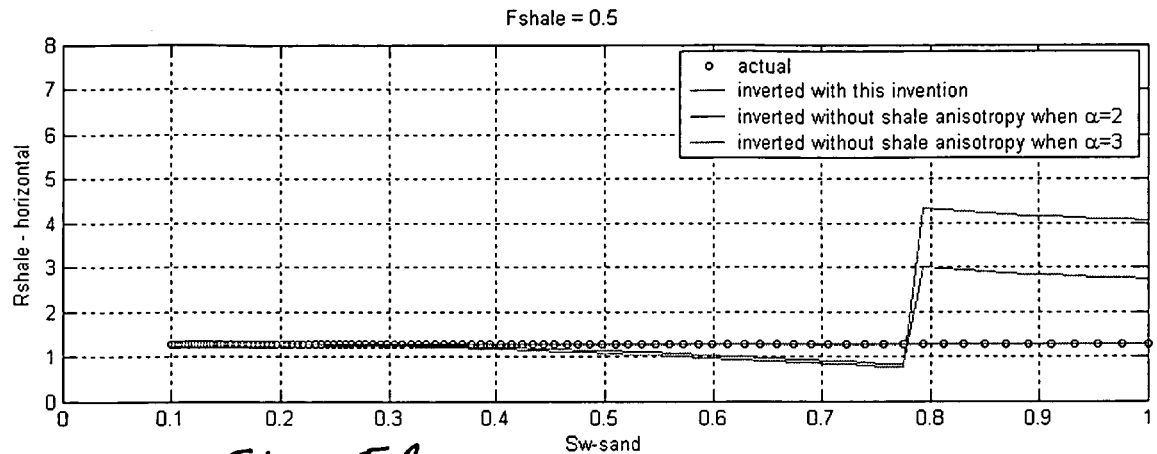
FIGS. 5A, 5B, and 5C are graphs of the horizontal shale resistivity, the vertical shale resistivity, and sand resistivity, respectively, plotted against the water saturation of the sand as determined using the present invention.
Figure 5B:
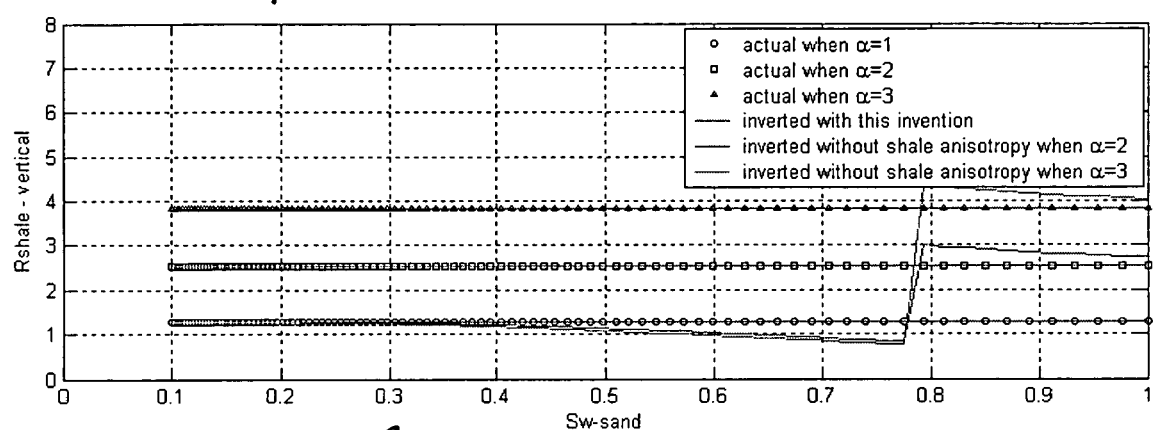
Figure 5C:
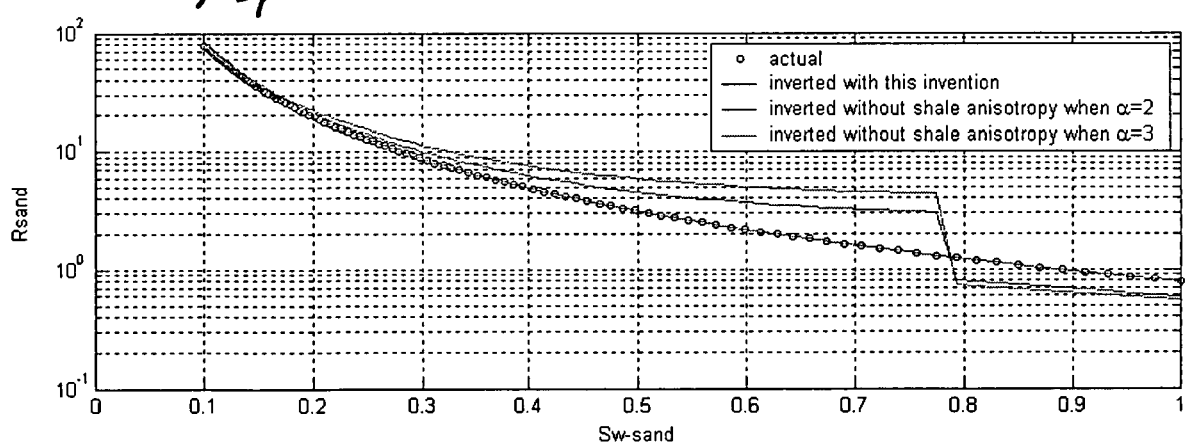
Figure 6A:
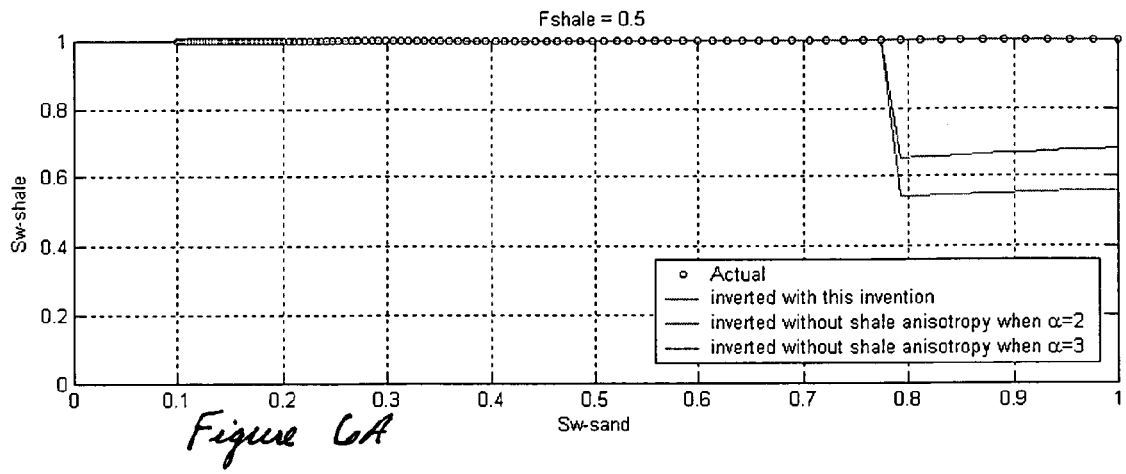
FIGS. 6A, 6B, and 6C are graphs of the water saturation of the shale, the water saturation of the sand, and the total water saturation of the formation, respectively, plotted against the water saturation of the sand as determined using the present invention.
Figure 6B:
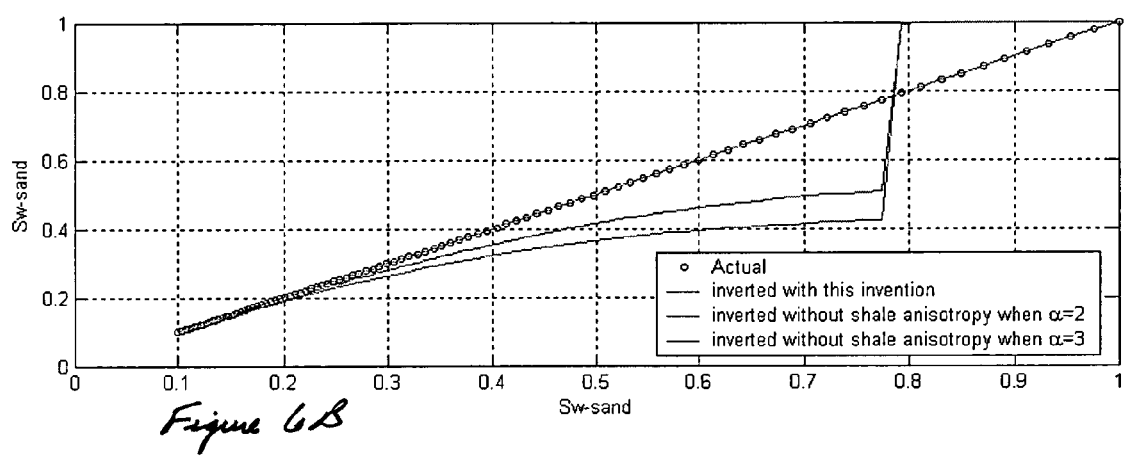
Figure 6C:
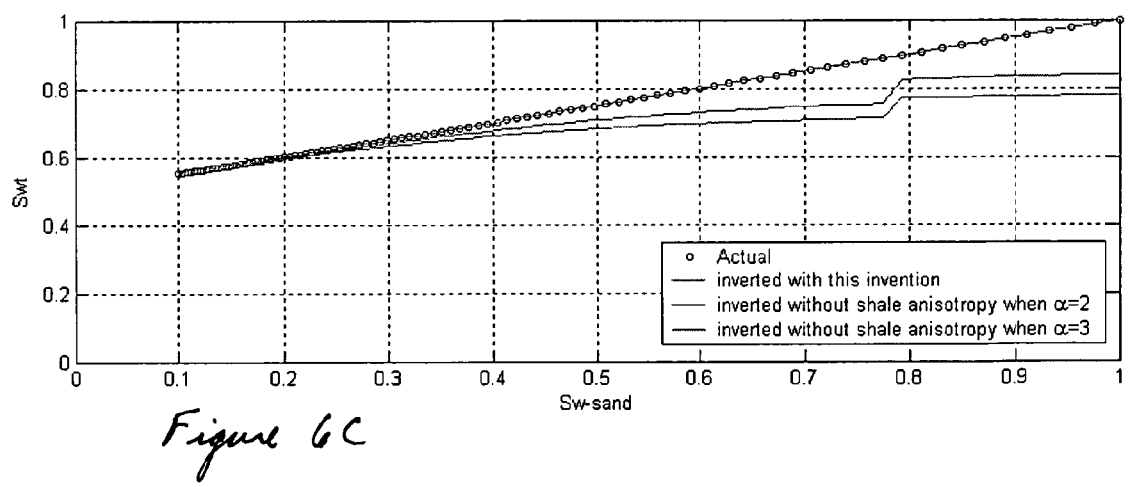

Results for the computation of the horizontal and vertical shale resistivities and the horizontal sand resistivity as a function of the sand/water saturation is presented in FIG. 5. Results for the computation of the shale, sand, and total water saturation are presented in FIG. 6. FIG. 5 shows that not taking the shale anisotropy into account will lead to a sand resistivity value higher than it should be and a higher shale resistivity when the water saturation $S_w$ in the sand is low. As a consequence, inverting 3D resistivity data without taking the shale anisotropy into account may lead to a false conclusion of oil in the shale (see top plot in FIG. 6) and too optimistic a total water saturation $S_{w-total}$ when the sand is at low hydrocarbon saturation (at or near a transition zone, for example).

The present method gives the correct shale and sand resistivities in laminated shale-sand formations when the shale are anisotropic (and, of course, also when they are isotropic). Using 3D resistivity logging techniques, one can get the correct shale and sand resistivities, even if the shale are anisotropic, by using equations (6) and (7), and using equation (8) to decide the proper sign to use in equations (6) and (7), as shown below:

$$R_{sand} = \frac{R_v + R_h \cdot (1 - f_{shale})^2 - \alpha \cdot R_h \cdot f_{shale}^2 - \sqrt{\begin{array}{c}[R_v + R_h \cdot (f_{shale} \cdot (f_{shale} \cdot (1 - \alpha) - 2) + 1)]^2 - \\ 4 \cdot (1 - f_{shale})^2 \cdot R_h \cdot R_v\end{array}}}{2(1 - f_{shale})}$$

$$R_{shale-h=} = \frac{R_v - R_h \cdot (1 - f_{shale})^2 + \alpha \cdot R_h \cdot f_{shale}^2 + \sqrt{\begin{array}{c}[R_v + R_h \cdot (f_{shale} \cdot (f_{shale}(\alpha - 1) + 2) - 1)]^2 - \\ 4 \cdot \alpha \cdot f_{shale}^2 \cdot R_h \cdot R_v\end{array}}}{2 \cdot \alpha \cdot f_{shale}} \text{ when}$$

$$R_h \leq \frac{R_{shale}^2}{f_{shale} \cdot \alpha \cdot R_{shale-h} + R_{shale-h} \cdot \sqrt{\alpha \cdot (1 - f_{shale})^2}} \text{ and}$$

$$R_{sand} = \frac{R_v + R_h \cdot (1 - f_{shale})^2 - \alpha \cdot R_h \cdot f_{shale}^2 + \sqrt{\begin{array}{c}[R_v + R_h \cdot (f_{shale} \cdot (f_{shale} \cdot (1 - \alpha) - 2) + 1)]^2 - \\ 4 \cdot (1 - f_{shale})^2 \cdot R_h \cdot R_v\end{array}}}{2(1 - f_{shale})}$$

$$R_{shale-h=} = \frac{R_v - R_h \cdot (1 - f_{shale})^2 + \alpha \cdot R_h \cdot f_{shale}^2 - \sqrt{\begin{array}{c}[R_v + R_h \cdot (f_{shale} \cdot (f_{shale}(\alpha - 1) + 2) - 1)]^2 - \\ 4 \cdot \alpha \cdot f_{shale}^2 \cdot R_h \cdot R_v\end{array}}}{2 \cdot \alpha \cdot f_{shale}} \text{ when}$$

$$R_h > \frac{R_{shale}^2}{f_{shale} \cdot \alpha \cdot R_{shale-h} + R_{shale-h} \cdot \sqrt{\alpha \cdot (1 - f_{shale})^2}}$$

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method to determine the water saturation of a laminated formation having a first layer-type and a second layer-type, comprising:
   disposing one or more logging tools in a wellbore;
   measuring the formation vertical and horizontal resistivities and at least one of the first layer-type and second layer-type volumes to produce a set of formation measurements using the one or more logging tools;
   modeling the formation as having one or more isotropic first layer-type layers and one or more anisotropic second layer-type layers;
   determining from the formation model and the set of formation measurements the resistivity of the isotropic first layer-type and the horizontal resistivity of the anisotropic second layer-type; and
   determining the formation water saturation using the resistivity of the isotropic first layer-type and the horizontal resistivity of the anisotropic second layer-type.

2. The method of claim 1 in which the modeling the formation includes representing the formation vertical resistivity as a series model and the formation horizontal resistivity as a parallel model.

3. The method of claim 2 in which the series model includes computing an arithmetic mean using each layer's vertical resistivity and the parallel model includes computing a harmonic mean using each layer's horizontal resistivity.

4. The method of claim 1 in which determining the resistivity of the isotropic first layer-type and the horizontal resistivity of the anisotropic second layer-type includes determining the proper sign of a first term used in the computation of the resistivity of the isotropic first layer-type and the proper sign of a second term used in the computation of the horizontal resistivity of the anisotropic second layer-type.

5. The method of claim 4 in which the isotropic first layer-type is a sand and the anisotropic second layer-type is a shale.

6. The method of claim 4 in which determining the proper sign of the first term used in the computation of the resistivity of the isotropic first layer-type and the proper sign of the second term used in the computation of the horizontal resistivity of the anisotropic second layer-type includes computing a limit value for the formation horizontal resistivity and comparing the measured formation horizontal resistivity to the limit value.

7. The method of claim 6 in which the isotropic first layer-type is a sand and the anisotropic second layer-type is a shale.

8. The method of claim 1 in which determining the formation water saturation includes computing the water saturation of the isotropic first layer-type, the water saturation of the anisotropic second layer-type, the total water saturation, or any combination of the three.

9. The method of claim 8 in which the isotropic first layer-type is a sand and the anisotropic second layer-type is a shale.

10. The method of claim 8 further comprising using the resistivity of the formation water and the porosity of the isotropic first layer-type to determine the water saturation of the isotropic first layer-type.

11. The method of claim 10 in which the isotropic first layer-type is a sand.

12. The method of claim 8 further comprising using the resistivity of the formation water and the porosity of the anisotropic second layer-type to determine the water saturation of the anisotropic second layer-type.

13. The method of claim 12 in which the anisotropic second layer-type is a shale.

14. The method of claim 1 in which the determining the formation water saturation includes using a water saturation model selected from the group comprising of a dual water model, the Waxman-Smits equation, and Archie's law.

15. The method of claim 1 in which the one or more logging tools are selected from the group consisting of nuclear magnetic resonance logging tools, nuclear logging tools, resistivity logging tools, high resolution resistivity imagers, gamma ray logging tools, and spectroscopy logging tools.

16. The method of claim 1 in which the isotropic first layer-type is a sand and the anisotropic second layer-type is a shale.

* * * * *